United States Patent
Jordan et al.

(10) Patent No.: US 9,273,289 B2
(45) Date of Patent: Mar. 1, 2016

(54) DEPLETION OF HOST CELL COMPONENTS FROM LIVE VECTOR VACCINES

(75) Inventors: Ingo Jordan, Berlin (DE); Holger Bernhardt, Berlin (DE); Stefan Hartmann, Berlin (DE)

(73) Assignee: PROBIOGEN AG, Berlin (DE)

( * ) Notice: Subject to any disclaimer, the term of this patent is extended or adjusted under 35 U.S.C. 154(b) by 8 days.

(21) Appl. No.: 13/988,986

(22) PCT Filed: Nov. 23, 2011

(86) PCT No.: PCT/EP2011/005901
§ 371 (c)(1),
(2), (4) Date: Jun. 26, 2013

(87) PCT Pub. No.: WO2012/069190
PCT Pub. Date: May 31, 2012

(65) Prior Publication Data
US 2013/0273636 A1  Oct. 17, 2013

Related U.S. Application Data

(60) Provisional application No. 61/417,319, filed on Nov. 26, 2010.

(51) Int. Cl.
*C12N 7/02*  (2006.01)

(52) U.S. Cl.
CPC ........ *C12N 7/02* (2013.01); *C12N 2710/24151* (2013.01)

(58) Field of Classification Search
None
See application file for complete search history.

(56) References Cited

U.S. PATENT DOCUMENTS

| 2002/0127582 A1* | 9/2002 | Atkinson et al. ................... 435/6 |
| 2009/0017523 A1* | 1/2009 | Weggeman et al. .......... 435/239 |
| 2009/0022759 A1* | 1/2009 | Burgert et al. ............. 424/199.1 |

FOREIGN PATENT DOCUMENTS

WO  01/48155  7/2001

OTHER PUBLICATIONS

Specht et al. Densonucleosis virus purification by ion exchange membranes. Biotechnol Bioeng. Nov. 20, 2004;88(4):465-73.*
Goerke et al. Development of a novel adenovirus purification process utilizing selective precipitation of cellular DNA. Biotechnol Bioeng. Jul. 5, 2005;91(1):12-21.*
"Phosphate buffered saline" (http://en.wikipedia.org/wiki/Phosphate_buffered_saline).*
DMEM formula. http://www.sigmaaldrich.com/content/dam/sigma-aldrich/docs/Sigma/Formulation/d6429for.pdf. undated.*
Michael W. Wolff et al: "Purification of cell culture-derived modified vaccinia ankara virus by pseudo-affinity membrane adsorbers and hydrophobic interaction chromatography", Biotechnology and Bioengineering, vol. 107, No. 2, Oct. 1, 2010, pp. 312-320.
Michael W. Wolff et al: "Capturing of cell culture-derived modified Vaccinia Ankara virus by ion exchange and pseudo-affinity membrane adsorbers", Biotechnology and Bioengineering, vol. 1 05, No. 4, Mar. 1, 2010, pp. 761-769.
Lars Opitz et al: "Sulfated membrane adsorbers for economic pseudo-affinity capture of influenza virus particles", Biotechnology and Bioengineering, vol. 103, No. 6, Aug. 15, 2009, pp. 1144-1154.
International Preliminary Report on Patentability for PCT/EP2011/005901, mailed May 28, 2013.
Zurbriggen, S., Tobler, K., Abril, C. et al. Isolation of sabin-like polioviruses from wastewater in a country using inactivated polio vaccine. Appl Environ Microbiol 2008, 74(18), 5608-5614.
Marris, E. Dramatic rescue relieves rare case of smallpox infection. Nat Med 2007, 13(5), 517.
Parrino, J. & Graham, B.S. Smallpox vaccines: Past, present, and future. J Allergy Clin Immunol 2006, 118(6), 1320-1326.
Excler, J.L., Parks, C.L., Ackland, J., Rees, H., Gust, I.D. & Koff, W.C. Replicating viral vectors as HIV vaccines: Summary report from the IAVI-sponsored satellite symposium at the AIDS vaccine 2009 conference. Biologicals 2010, 38(4), 511-521.
Plotkin, S.A. Vaccines: the fourth century. Clin Vaccine Immunol 2009, 16(12), 1709-1719.
Cebere, I., Dorrell, L., McShane, H. et al. Phase I clinical trial safety of DNA- and modified virus Ankara-vectored human immunodeficiency virus type 1 (HIV-1) vaccines administered alone and in a prime-boost regime to healthy HIV-1-uninfected volunteers. Vaccine 2006, 24(4), 417-425.
Dorrell, L., Williams, P., Suttill, A. et al. Safety and tolerability of recombinant modified vaccinia virus Ankara expressing an HIV-1 gag/multiepitope immunogen (MVA.HIVA) in HIV-1-infected persons receiving combination antiretroviral therapy. Vaccine 2007, 25(17), 3277-3283.
Jin, X., Ramanathan, M., Jr., Barsoum, S. et al. Safety and immunogenicity of ALVAC vCP1452 and recombinant gp160 in newly human immunodeficiency virus type 1-infected patients treated with prolonged highly active antiretroviral therapy. J Virol 2002, 76(5), 2206-2216.
Webster, D.P., Dunachie, S., Vuola, J.M. et al. Enhanced T cell-mediated protection against malaria in human challenges by using the recombinant poxviruses FP9 and modified vaccinia virus Ankara. Proc Natl Acad Sci U S A 2005, 102(13), 4836-4841.
Drillien, R., Spehner, D. & Hanau, D. Modified vaccinia virus Ankara induces moderate activation of human dendritic cells. J Gen Virol 2004, 85(Pt 8), 2167-2175.

(Continued)

*Primary Examiner* — Stacy B Chen
*Assistant Examiner* — Nick Zou
(74) *Attorney, Agent, or Firm* — McDonnell Boehnen Hulbert & Berghoff LLP

(57) ABSTRACT

It is desirable to produce live vaccines, which are highly attenuated and which do only contain minimal or no animal-derived components. The production of highly attenuated live viruses can be better achieved when using specifically designed cell lines as producer substrate as opposed to using less defined primary cells. However, live viruses, thus produced comprise undesirable components from the cell lines and cell culture. The present invention relates to methods of production and purification of live enveloped viruses, which are suitable for vaccination.

15 Claims, 7 Drawing Sheets

(56) References Cited

OTHER PUBLICATIONS

Liu, L., Chavan, R. & Feinberg, M.B. Dendritic cells are preferentially targeted among hematolymphocytes by Modified Vaccinia Virus Ankara and play a key role in the induction of virus-specific T cell responses in vivo. BMC Immunol 2008, 9, 15.

Ryan, E.J., Harenberg, A. & Burdin, N. The Canarypox-virus vaccine vector ALVAC triggers the release of IFN-gamma by Natural Killer (NK) cells enhancing Th1 polarization. Vaccine 2007, 25(17), 3380-3390.

Sutter, G. & Moss, B. Nonreplicating vaccinia vector efficiently expresses recombinant genes. Proc Natl Acad Sci U S A 1992, 89(22), 10847-10851.

Sutter, G., Wyatt, L.S., Foley, P.L., Bennink, J.R. & Moss, B. A recombinant vector derived from the host range-restricted and highly attenuated MVA strain of vaccinia virus stimulates protective immunity in mice to influenza virus. Vaccine 1994, 12(11), 1032-1040.

Coulibaly, S., Bruhl, P., Mayrhofer, J., Schmid, K., Gerencer, M. & Falkner, F.G. The nonreplicating smallpox candidate vaccines defective vaccinia Lister (dVV-L) and modified vaccinia Ankara (MVA) elicit robust long-term protection. Virology 2005, 341(1), 91-101.

Gilbert, S.C., Moorthy, V.S., Andrews, L. et al. Synergistic DNA-MVA prime-boost vaccination regimes for malaria and tuberculosis. Vaccine 2006, 24(21), 4554-4561.

Rotz, L.D., Dotson, D.A., Damon, I.K. & Becher, J.A. Vaccinia (smallpox) vaccine: recommendations of the Advisory Committee on Immunization Practices (ACIP), 2001. MMWR Recomm Rep 2001, 50(RR-10), 1-25; quiz CE21-27.

Monto, A.S., Maassab, H.F. & Bryan, E.R. Relative efficacy of embryonated eggs and cell culture for isolation of contemporary influenza viruses. J Clin Microbiol 1981, 13(1), 233-235.

White, D.O. & Fazekas De St Groth, S. Variation of host resistance to influenza viruses in the allantois. J Hyg (Lond) 1959, 57(1), 123-133.

Philipp, H.C. & Kolla, I. Laboratory host systems for extraneous agent testing in avian live virus vaccines: problems encountered. Biologicals 2010, 38(3), 350-351.

Enserink, M. Influenza. Crisis underscores fragility of vaccine production system. Science 2004, 306(5695), 385.

Jordan, I., Vos, A., Beilfuss, S., Neubert, A., Breul, S. & Sandig, V. An avian cell line designed for production of highly attenuated viruses. Vaccine 2009, 27(5), 748-756.

Manohar, M., Orrison, B., Peden, K. & Lewis, A.M., Jr. Assessing the tumorigenic phenotype of VERO cells in adult and newborn nude mice. Biologicals 2008, 36(1), 65-72.

Cyrklaff, M., Risco, C., Fernandez, J.J. et al. Cryo-electron tomography of vaccinia virus. Proc Natl Acad Sci U S A 2005, 102(8), 2772-2777.

Francis, D.P. Successes and failures: Worldwide vaccine development and application. Biologicals 2010, 38(5), 523-528.

Farrah, S.R., Preston, D.R., Toranzos, G.A., Girard, M., Erdos, G.A. & Vasuhdivan, V. Use of modified diatomaceous earth for removal and recovery of viruses in water. Appl Environ Microbiol 1991, 57(9), 2502-2506.

Carter, M.J. & Milton, I.D. An inexpensive and simple method for DNA purifications on silica particles. Nucleic Acids Res 1993, 21(4), 1044.

\* cited by examiner

DEPLETION OF HOST CELL COMPONENTS FROM LIVE VECTOR VACCINES

It is desirable to produce live vaccines, which are highly attenuated and which do only contain minimal or no animal-derived components. The production of highly attenuated live viruses can be better achieved when using specifically designed cell lines as producer substrate as opposed to using less defined primary cells. However, live viruses, thus produced comprise undesirable components from the cell lines and cell culture. The present invention relates to methods of production and purification of live enveloped viruses, which are suitable for vaccination.

BACKGROUND OF THE INVENTION

Although vaccines are widely used and protect against a surprisingly broad spectrum of infectious diseases, protective or therapeutic immunity still cannot be raised against a number of latent and chronic pathogens including *Mycobacterium tuberculosis*, human immunodeficiency virus, hepatitis C virus, and the *Plasmodium* protists causing malaria. Conventional approaches that mainly elicit antibody responses have not been successful in providing protective or therapeutic immunity. It is believed that this is due to the fact that epitopes are variable, frequently masked or protected by microbial decoys, or because the dynamic of the infectious cycle may seclude the pathogen into compartments not accessible to antibodies.

Compared to vaccination with inactivated virions or purified subunits, live vaccines induce a broad response that also involves the cellular compartment of the immune system. For safe limitation of a natural infection the vaccine strains are attenuated, but for certain viruses there is a risk of reversion to pathogenic strains (Zurbriggen et al. 2008 in Appl Environ Microbiol 74, 5608-5614) or potential residual virulence for some vaccinees or their contact persons (Marris 2007 in Nat Med 13, 517). In addition, compared to the smallpox eradication program of the 1970s, any pathogenic potential of a vaccine vector may be amplified by the increases in international travel and numbers of immunocompromized individuals. Thus, a greater degree of safety is highly desirable in any novel live vectors (Parrino and Graham 2006 in J Allergy Clin Immunol 118, 1320-1326).

Modern vectored vaccines (Excler et al. 2010 in Biologicals 38, 511-521; Plotkin 2009 in Clin Vaccine Immunol 16, 1709-1719) combine the advantages of live vaccines with the strong safety profile inherent to the highly attenuated vectors, and thus may provide novel therapeutic or protective approaches. Promising vectors are replication deficient alphavirus vectors and highly attenuated poxviruses including modified vaccinia Ankara (MVA), fowlpox (such as strain FP9), and canarypox (ALVAC). These vectors do not replicate in human cells and can therefore be safely given even to immunocompromised recipients (for example (Cebere et al. 2006 in Vaccine 24, 417-425; Dorrell et al. 2007 in Vaccine 25, 3277-3283; Jin et al. 2002 in J Virol 76, 2206-2216; Webster et al. 2005 in Proc Natl Acad Sci USA 102, 4836-4841). They can accommodate large inserts and provide a strong stimulation of the immune system against the vectored antigen (for example (Drillien et al. 2004 in J Gen Virol 85, 2167-2175; Liu et al. 2008 in BMC Immunol 9, 15; Ryan et al. 2007 in Vaccine 25, 3380-3390; Sutter and Moss 1992 in Proc Natl Acad Sci USA 89, 10847-10851; Sutter et al. 1994 in Vaccine 12, 1032-1040).

Disadvantages are directly related to the beneficial properties: the high degree of attenuation necessitates very high numbers of infectious units per dose for full efficacy, and because host range is restricted production requires improved cellular substrates (in some cases from avian donors) or special packaging cell lines.

To illustrate the extent of the industrial challenge with precise numbers and MVA as an example (without limiting this application to MVA only):

Dose requirement is estimated at $10^8$ infectious units of MVA per vaccination (Coulibaly et al. 2005 in Virology 341, 91-101; Gilbert et al. 2006 in Vaccine 24, 4554-4561). For global programs against complex infectious diseases such as HIV or tuberculosis hundreds of million of doses of the highly attenuated poxviruses may be required annually. For comparison, lesser attenuated strains also produced in avian cells include vaccines against measles, mumps and yellow fever; these require only $10^3$, $2\times10^4$ and $5.5\times10^4$ infectious units per dose, respectively (information from the package inserts of YF-VAX from Sanofi Pasteur and M-M-R II from Merck). The protective dose of the vaccinia strain Dryvax in routine vaccination against smallpox is $2.5\times10^5$ pfu (Rotz et al. 2001 in MMWR Recomm Rep 50, 1-25; quiz CE21-27), 400 fold lower than the dose recommended for MVA.

However, production of MVA depends on avian cells. Currently, vaccine strains adapted to avian hosts are produced only in embryonated chicken eggs or on fibroblasts prepared from such eggs, a venerable technology but also associated with certain disadvantages. Because primary cells suffer senescence within few passages they have to be supplied continuously. Differences in timing and preparation may lead to lot variations (Monto et al. 1981 in J Clin Microbiol 13, 233-235; White and Fazekas De St Groth 1959 in J Hyg (Lond) 57, 123-133). The embryonated eggs as source for the fibroblasts are from expensive SPF (specific pathogen free) flocks. The SPF status requires elaborate husbandry, and transport of material across country borders complicates logistics and also cause shortages. Even with SPF precautions in place, contamination with extraneous agents cannot always be prevented. Because time from collection of the embryonated eggs to production of the vaccine is short, testing for extraneous agents is performed on the final bulk (Philipp and Kolla 2010 in Biologicals 38, 350-351). Occasionally, complete vaccine lots have to be discarded when contamination is confirmed by quality testing (Enserink 2004 in Science 306, 385).

Finally, with primary cells it is also not possible to stably express transgenes that may further enhance production of highly attenuated viruses or allow packaging of replication-deficient vectors.

The present inventors have immortalized primary cells from a muscovy duck embryo to replace primary cells as substrate (Jordan et al. 2009 in Vaccine 27, 748-756) and have developed a chemically defined production process for viral vaccines based on this cell line. They have also generated packaging cells based on this cell line (WO 2009/156155). With this technology available one can now expand the development towards vaccine production from a continuous culture in a chemically defined medium and infected with a modern viral vector.

The main challenge at this point is to meet health regulatory guidelines. One of the guidelines that applies here is the World Health Organization Technical Report Series 878 from the year 1998. It is suggested (see the section starting on page 26) that a level of 10 ng of DNA would be acceptable per dose of live vector.

To the knowledge of the present inventors, there are presently no approved live vaccines produced from continuous cell lines. Currently approved live vaccines are produced on primary cells such as chicken embryo fibroblasts (attenuated measles, mumps, yellow fever and influenza viruses), MRC-5 or WI-38 human diploid cell preparations (rubella and varicella viruses), and Vero cells (vaccinia virus and rotavirus). For these cell lines, regulatory procedures with respect to host cell derived components are less stringent, mainly due to the large body of experience that exist. However, as discussed above for chicken embryo fibroblasts, any primary cell preparation has considerable disadvantages and limits in supply. This also applies to Vero cells that may be considered a continuous cell line. However, this line is acceptable for vaccine production only at low cell passage levels (Manohar et al. 2008 in Biologicals 36, 65-72).

Modern continuous cell lines overcome many disadvantages of primary cells but introduce a new challenge, the requirement to define and then to minimize the risk that may be associated with host cell components carried over into the vaccine preparation. Accordingly, the present inventors provide methods of production and purification of live vaccines, which overcome problems of prior art vaccines and provide further advantages.

SUMMARY OF THE INVENTION

In a first aspect, the present invention relates to a method of virus purification comprising the steps of
(i) adding one or more chaotropic salts and/or polar or charged macromolecules to a virus producing cell prior to cell lysis,
(ii) lysing said virus producing cell, and
(iii) separating said virus from at least part of the non-viral substances comprised in said virus producing cell or its cell culture medium.

In a second aspect, the present invention relates to a method of virus purification comprising the steps of
(i) lysing a virus producing cell, and
(ii) applying the lysate of said virus producing cell onto a siliceous substance.

In a third aspect, the present invention relates to a virus or a plurality of viruses of a purity obtainable with the methods according to the first and/or the second aspect. In a fourth aspect, the present invention relates to the virus or plurality of viruses of the third aspect for inducing an immune response. In a fifth aspect, the present invention relates to the virus or plurality of viruses of the third and/or fourth aspect for the prevention or treatment of an infection.

This summary of the invention does not describe all features of the invention.

DETAILED DESCRIPTION OF THE INVENTION

1. Disclaimer

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IU-PAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. The focus of the invention rests on removal of DNA as the most relevant contaminant. However, removal of host cell derived protein is also of importance and specifically considered in example 1. With successful removal of DNA the depletion of host cell derived protein often is a highly desired side effect.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

As used in this specification and the appended claims, the singular forms "a", "an", and "the" include plural referents, unless the content clearly dictates otherwise.

2. Focus

Herein, the present inventors disclose results and describe developments that can be applied to reduce host cell contamination and thus contribute to the solutions of a significant challenge in the field of live vaccine and/or vector production from a continuous cell line.

As endogenous parasites, viruses depend on host cell functions for progeny formation. In their life cycle, viruses can incorporate host cell derived components, for example ribosomes into arenaviral virions or cyclophilin A into HIV particles. Such incorporated cellular factors may be beneficial in the first steps of re-infection (ribosomes) or even essential (cyclophilin A) for virus maturation. They should not be removed by the purification procedure. The methods described here exert a transforming activity on the virus suspension after viral morphogenesis has been completed and therefore do not affect beneficial integral components of the virus particles.

Virions may also associate unspecifically with cellular components. The accessible surface of infectious viruses for this interaction can be either purely proteinaceous (for example adenoviruses and picornaviruses) or based on a lipid membrane (for example alphavirus, rabies and vaccinia viruses). The latter are termed enveloped viruses, and for this group of viruses purification is especially difficult: the viral envelope may contain a highly complex and mobile collection of disparate molecules that range from sulfogroups in glycoproteins to aliphatic alcohols in sphingolipids that each or in combination present a range of electrostatic, van der Waals, or hydrophobic interaction surfaces for various binding partners derived from the culture medium itself, producer cells, or other viral particles. The present invention contributes production and purification processes essential in adaptation to this chemistry.

A typical crude lysate of MVA-infected cells contains $2.5 \times 10^5$ ng/mL DNA and $3.0 \times 10^9$ pfu/mL MVA. Using $1 \times 10^8$ pfu as vaccine dose one usually obtains 8300 ng of DNA per dose, more than 800-fold in excess of the amount of DNA admissible according to the WHO guideline. This DNA contamination as well as other contaminations are an enormous challenge that must be solved before vectorial vaccines from any continuous cell line can be produced and used in large scale, which is required for global vaccination against highly destructive infectious diseases.

DNA nucleases such as Benzonase® can help to reduce amount and size of DNA but are expensive and not fully effective due to steric hindrance if the nucleic acids associate with debris or viral particles. Furthermore, any nuclease that has been added to the preparation must also be removed after treatment is complete to meet regulatory requirements. Thus, even when enzymatic hydrolysis of DNA comprised in the lysate, reduction of DNA to acceptable levels remains a continuing problem that must be solved.

The present inventors discovered and describe herein a combination of procedures that allow the prevention of transfer of contaminants into virus preparations. Specific chemicals and changes in osmolarity and pH are used to disrupt complexes between virions and host cell or host cell debris, preferably after lysis.

The present inventors also determined that complex formation between contaminants and viral envelope can be prevented. This can be achieved by initiating harvesting at a time where the host cell still is largely intact, i.e. when only little or no lysis of the host cell has occurred, which may occur during propagation, e.g. due to lysis during viral budding or because of senescence and/or apoptosis. In such a setup, the first step just immediate to purification is the addition of masking compounds such as chaotropic salts and/or polar or charged macromolecules that associate with infectious virus or with the contaminants. These masking compounds protect any binding sites that mediate association of virions with host cell factors or debris from downstream processing.

3. Embodiments

Accordingly, in a first aspect, the present invention relates to a method for virus purification comprising the steps of
 (i) adding one or more chaotropic salts and/or polar or charged macromolecules to a virus producing cell prior to cell lysis,
 (ii) lysing said virus producing cell, and
 (iii) separating said virus from at least part of the non-viral substances comprised in said virus producing cell or its cell culture medium.

For separating virus from undesired impurities, the present inventors resorted to the unusual step to use diatomaceous earth to purify rather than to remove virus.

Accordingly, in a second aspect, the present invention relates to a method for virus purification comprising the steps of
 (i) lysing a virus producing cell, and
 (ii) applying the lysate of said virus producing cell onto a siliceous substance.

Further, in a preferred embodiment, step (iii) of the method of the first aspect is carried out by filtration over a siliceous substance. It is also preferred for the second aspect that the lysate is separated from the siliceous substance, preferably by filtration.

4. Siliceous Substances

The siliceous substance is preferably selected from the group consisting of diatomaceous earth, acid washed diatomaceous earth, acid etched diatomaceous earth, or diatomaceous earth treated with a silane. In a preferred embodiment, 0.1 g to 20 g, preferably 3 g to 10 g of siliceous substance, preferably diatomaceous earth, per mg of non-viral substances, preferably of non-viral intra- or extracellular substance, is used. Most preferably the amount of siliceous substance is determined on the basis of the DNA content in the lysis solution and 0.1 g to 20 g, preferably 3 g to 10 g of siliceous substance is used per mg of DNA in the lysis solution. It is preferred that the lysate is incubated, preferably with agitation with the siliceous substance. If the lysate is filtered over the siliceous substance this is preferably achieved by applying the siliceous substance to a funnel or other retaining means with a pore width that is smaller then the average particle width of the respective siliceous substance used.

5. Chaotropic Substances and Polar or Charged Macromolecules

To adjust conditions towards preferential binding of DNA compared to virus, the present inventors introduced chaotropic salts and/or polar or charged macromolecules into the preparation. Therefore, in a preferred embodiment, the method of the second aspect comprises prior or after step (i) the addition of one or more chaotropic salts and/or polar or charged macromolecules. Such additives are expected to kill a majority of the infectious viruses, rendering the preparation unsuitable for vectorial vaccine application. One reason is that, by definition, chaotropes and polar or charged macromolecules facilitate formation of a solvation shell around viral and non-viral components. Such a solvation shell can also affect virus integrity or receptor recognition at the host plasma membrane.

Surprisingly, the inventors found a balance of these opposing requirements (denoted as a "mild chaotropic environment") that allow recovery of infectious units with very high yields and at the same time removal of contaminants for further downstream processing. This discovery prevents blocking of pores in the chromatography material and prevents masking of functional groups in the chromatography matrix required for exchange or affinity purification. Thus, this step also significantly increases efficiency of further processing of the lysate. Chaotrophic salts that can be used to create "mild chaotrophic environments" are those salts that shield charges and prevent the stabilization of salt bridges, e.g. urea, thiourea, guanidinium chloride, lithium perchlorate, sodium bromide and potassium chloride. These are well known in the art. However, to create the desired mild chaotrophic environment, the chaotrophic salts are added in a concentration, which do not reduce infectivity of the isolated virus. In the embodiment wherein the chaotrophic salt is added already during incubation it is preferred that the amount of chaotrophic salt is chosen in such that cell lysis is not significantly increased.

In a preferred embodiment of the method of the first and second aspect, the chaotropic salts and/or polar or charged macromolecules bind to one or more of the non-viral substances, preferably intra- or extracellular substances and/or to said virus.

In a particular preferred embodiment the chaotropic salts capable of creating a mild chaotrophic environment are NaBr and/or KCl and/or urea, optionally in combination with dextran sulphate and/or polyphosphoric acid and/or polyvinylpyrollidon. Preferably, the concentration of the chaotropic salts and/or polar or charged macromolecules is such that the virus remains substantially intact and/or infectious. Substantially intact means that the half-life of the virus in serum, preferably human serum is at least 10%, at least 20%, at least 30%, at least 40%, at least 50%, at least 60%, at least 70%, at least 80%, at least 90%, or at least 95% of the half-life of the virus not treated with the chaotropic salts and/or polar or charged macromolecules. More preferably, the concentration of NaBr is between 5 mM and 750 mM, between 25 mM and 700 mM, between 50 mM and 650 mM, between 75 mM and 600 mM, between 100 mM and 550 mM, between 125 mM and 500 mM, between 150 mM and 450 mM, between 175 mM and 400 mM, or preferably between 200 mM and 350 mM. Preferably, the pH is in the range of 7.4 to 8.0, 6.0 to 6.5, 6.5 to 6.8, 6.8 to 7.2, more preferably 7.2 to 7.4.

Preferably, the concentration of KCl is between 1 mM and 750 mM, between 15 mM and 700 mM, between 30 mM and 650 mM, between 45 mM and 600 mM, between 60 mM and 550 mM, between 75 mM and 500 mM, between 90 mM and 450 mM, between 105 mM and 400 mM, or preferably between 120 mM and 350 mM. Preferably, the concentration of urea is between 0.2 mM and 2 M, between 5 mM and 1 M, or between 100 mM and 500 mM. Preferably, the concentration of dextran sulfate is between 5 mg/l and 1000 mg/l, between 10 mg/l and 800 mg/l, or preferably between 15 mg/l and 600 mg/l. Preferably, the concentration of polyphosphoric acid is between 0.1 mM and 100 mM, between 0.2 mM and 80 mM, or preferably between 0.3 mM and 60 mM. Preferably, the concentration of polyvinylpyrrolidon is between 0.2% and 10%, between 1% and 8%, between 2% and 6% between 3% and 4%. Preferably, the concentration of Tween-20 and/or octylphenoxypolythoxyethanol (IGEPAL) is between 0.05% and 0.25%, between 0.1% and 0.20%, or preferably between 0.13% and 0.17%, each. Preferably, the pH is in the range of 7.4 to 8.0, 6.0 to 6.5, 6.5 to 6.8, 6.8 to 7.2, more preferably 7.2 to 7.4.

6. Timing Details

Surprisingly, the present inventors found that it is also feasible to add one or more chaotropic salts and/or polar or charged macromolecules prior to lysis, e.g. preferably at the time of infection or immediately thereafter to achieve the effect of the invention. This was surprising since some of these substances have been used in downstream processing but yet are compatible with various stages of the production process where cell viability has to be sufficient for virus replication. Therefore, the chaotropic salts and/or polar or charged macromolecules are preferably added at the time of cell infection with the virus, immediately after the infection, at the time of peak virus production, or immediately prior to cell lysis.

7. Lysis Details

The skilled person knows how to lyse cells to release virus. However, depending on the respective host cell and respective live virus to be produced the method of lysis to effectively release virus from within or from the surface of the host cells, or from complexes with other virions or cellular debris may need to be optimized. Such optimization comprises the determination of the optimum method (for example, mechanically with ultrasound, blending or pressure homogenization through a narrow valve; or chemically with osmotic shock or detergent), optimum energy or reagent input (for example, intensity and duration of ultrasound treatment, or concentration of detergent), optimum pH and medium additive concentration (to maintain activity of virus liberated from the cellular environment, for example with pH 7.2 in presence of purified recombinant human albumin), and optimum time point (for example, lysis at a time where cell integrity and virus yields both are high, or at a time where cell integrity due to cytopathic effect already is very low).

The method of the invention is compatible with different methods of cell lysis. Preferred methods of lysis comprise disruption by treatment with one ore more cycles of temperature extremes, preferably temperatures of at least −85° C. and 25° C., detergent, preferably selected from the group consisting of Tween-20 and Triton X-100, ultrasound, and osmotic shock. Also contemplated is lysis using a cytopathic effect by allowing the infection to proceed past the peak yield, in presence or absence of masking compounds and in presence or absence of conditions that promote apoptosis. The advantage of apoptosis is that a natural process in cell cultures can be utilized for digestion of DNA and removal of protein while vector particles are protected by the envelope. Thus, in addition to the previously described method of lysis or as an alternative it is preferred that cell lysis is caused by one or more of the following necrosis or programmed cell death, preferably apoptosis.

The described method is compatible with infected cell suspensions harvested well after the infectious cycle has completed. For example, infectious titers for MVA peak 48 h after infection and harvest 72 h after infection yields lysates that can be further purified to our methods.

8. Further Processing Details

Additional manipulation of the lysate may be performed prior to concentration of infectious units by tangential flow filtration or continuous flow centrifugation, or prior to purification by chromatography via ion exchange, hydrophobic interaction or pseudoaffinity. One important observation was that infectious units of the highly attenuated poxviruses are lost by sedimentation also at low relative centrifugal forces. To clarify the lysate prior to chromatography, special filtration procedures are preferably carried out because these viruses are very large (flattened cylinders with 360 nm at the long axis (Cyrklaff et al. 2005 in Proc Natl Acad Sci USA 102, 2772-2777).

Accordingly, in a preferred embodiment the method of the invention further comprises after cell lysis one or more of the following additional purification steps in any order:
a) pre-filtration, e.g. tangential flow filtration, continuous flow filtration or filtration by macroporous materials such as monoliths,
b) chromatography, e.g. via ion exchange, hydrophobic interaction or pseudoaffinity,
c) centrifugation, e.g. continuous flow centrifugation, and
d) flocculation.

Preferably, said one or more additional purification steps are carried out prior to and/or after said step of virus filtration.

One particularly preferred embodiment of the present invention therefore is to filtrate a 10-fold concentrated, a 5-fold concentrated, singly concentrated or diluted lysate from infected cells in the presence of dextrane sulfate, NaBr and KCl through a silica matrix. This filtration step can be repeated one ore more times. Thereafter, a clear solution can be obtained and virus, preferably infectious virus, can be recovered from this preparation by said one or more additional purification steps, e.g. pseudoaffinity chromatography, tangential flow filtration, or continuous flow centrifugation.

9. Suitable Host Cells

In one embodiment of the method of the first and/or the second aspect of the invention, the virus producing cell is a dividing cell, preferably an immortal cell. Preferably, said virus producing cell in an uninfected state is derived from a continuous cell line such as AGE1.CR, AGE1.CR.pIX, AGE1.HN, AGE1.R06E, AGE1R05T, MDCK (Madin-Darby Canine Kidney; ATCC CCL 34), BHK (Baby Hamster Kidney) 21 (ATCC CCL-10)), BHK TK (ECACC No. 85011423), HEK (Human Embryonic Kidney) 293 (ATCC CRL 1573), or DF-1 (chicken fibroblast cell line developed by Doug Foster). The cell line AGE1.CR.pIX (17a11b) was deposited by ProBioGen, Goethestr. 54, 13086 Berlin, Germany, with the DSMZ-Deutsche Sammlung von Mikroorganismen und Zellkulturen GmbH, Mascheroder Weg 1b, 38124 Braunschweig, Germany on Nov. 24, 2005 under accession number DSM ACC2749. The cell line AGE1.HN (NC5T11 #34) was deposited by ProBioGen, Goethestr. 54, 13086 Berlin, Germany, with the DSMZ-Deutsche Sammlung von Mikroorganismen und Zellkulturen GmbH, Mascheroder Weg 1b, 38124 Braunschweig, Germany on Nov. 4, 2005 under accession number DSM ACC2744. The cell line AGE1R06E was deposited by ProBioGen, Goethestr. 54, 13086 Berlin, Germany, with the DSMZ-Deutsche Sammlung von Mikroorganismen und Zellkulturen GmbH, Mascheroder Weg 1b, 38124 Braunschweig, Germany on Apr. 3, 2008 under accession number DSM ACC2902.

In another embodiment, said virus producing cell is derived from Muscovy duck embryo or human neuronal tissue. The term "dividing cell" refers to a cell capable of proliferation. The term "immortal cell" or "continuous cell line" refers to a cell or cell line comprising cells capable of proliferation for at least 50 cell doublings, preferably at least 100 cell doublings and most preferably for an unlimited number of cell doublings.

10. Virus Details

In a further embodiment of the method of the first and/or the second aspect of the invention, said virus is attenuated and/or replication deficient. Attenuation and replication deficiency may be achieved by the removal of genes involved in pathogenicity and/or virus packaging within the host cell. These genes obviously depend on the specific virus used and are well known in the art. Preferably, said virus is a live or vectorial vaccine. In another embodiment, said virus is an enveloped virus. Preferably, said virus is selected from the group consisting of Poxyirdae, most preferably Modified Vaccinia Ankara (MVA), fowlpox, and canarypox; Togaviridae, most preferably alphaviruses and rubella virus; Mononegavirales, most preferably rabies virus and measles virus; Orthomyxoviridae, most preferrably influenza viruses A and B; and Herpesviridae, most preferrably varicella zoster virus and cytomegalovirus.

11. Contamination Details

In yet a further embodiment of the method of the first and/or the second aspect of the invention, said non-viral intra- or extracellular substances are undesirable for the application of the virus as a vaccine. In the most preferred embodiment, said non-viral intra- or extracellular substances are polynucleotides, preferably DNA, and more preferably cellular DNA, or host cell protein, or medium additives used in cultivation of the host cells or production of the viruses.

The life virus with increased purity and/or concentration will typically be recovered from the flow through. Accordingly, both methods preferably comprise the further step of recovering the flow through of the separation step (iii) of the first aspect or after the lysate has been applied toe siliceous substance in step (ii) of the second aspect.

12. Formulation Details

In a third aspect, the present invention relates to a virus or a plurality of viruses of a purity obtainable with the method of the first and/or the second aspect of the invention. Preferably, said purity is such that said virus or plurality of viruses is substantially free of said non-viral cell-derived substances, preferably polynucleotides and more preferably DNA. More preferably, the amount of virus is more than $1 \times 10^2$, $1 \times 10^3$, $1 \times 10^4$, $3.5 \times 10^4$, $1 \times 10^5$, $1 \times 10^6$, or preferably $1 \times 10^7$ pfu per ng of polynucleotides comprised in the cell medium or suspension derived from the cell medium, preferably DNA. The expression "in the medium" refers to the fact that the polynucleotide concentration does not include the viral genome contained in the viral particles. "Substantially free" means that at least 80%, at least 90%, at least 91%, at least 92%, at least 93%, at least 94%, at least 95%, at least 96%, at least 97%, at least 98%, or preferably at least 99%, 99.1%, 99.2%, 99.3%, 99.4%, 99.5%, 99.6%, 99.7%, 99.8%, or 99.9% of the non-viral substances comprised in the virus producing cell or its cell culture medium is removed.

In another embodiment, the virus or plurality of viruses of the third aspect is associated with said one or more chaotropic substances and/or polar or charged macromolecules.

BRIEF DESCRIPTION OF THE FIGURES

The following figures are merely illustrative of the present invention and should not be construed to limit the scope of the invention as indicated by the appended claims in any way.

EXAMPLES

Figure 1:
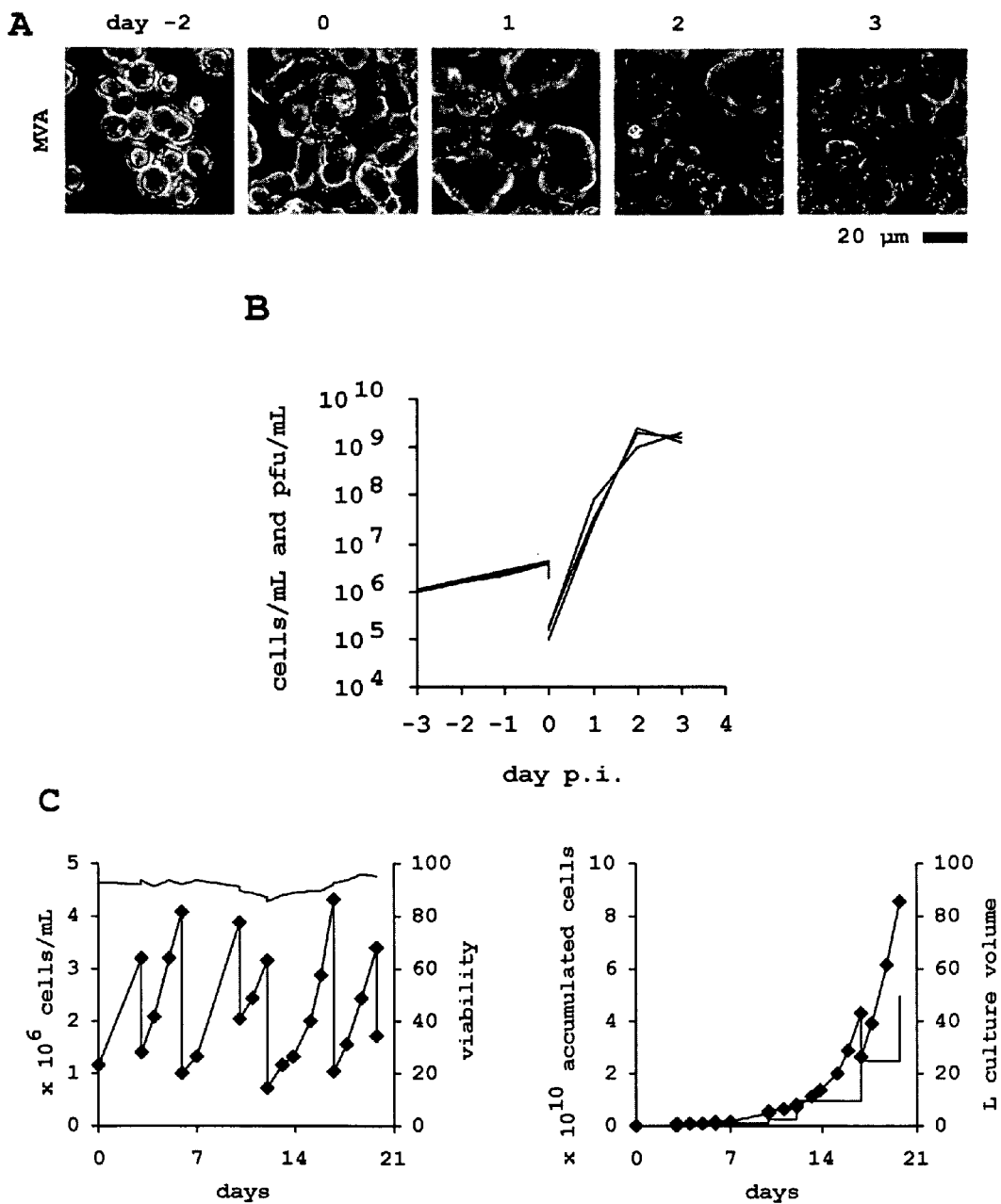
FIG. 1: Demonstration of the scalable virus production process in a bioreactor in a chemically defined media. Panel (A) shows appearance of the AGE1.CR continuous cell line in a chemically defined media at various stages of the bioreactor process for production of wildtype MVA. Day 0 refers to the time of infection, negative days for the proliferation phase and positive days for appearance until harvest. Panel (B) provides cell densities and infectious units at the described time points. Panel (C) demonstrates one beneficial property of the continuous cell line: such a substrate can be thawed from a cryovial and expanded within the production facility without need for external supply with exception of the pure chemical required to produce the culture medium.

The examples given below are for illustrative purposes only and do not limit the invention described above in any way.

Example 1

Production of Virus in a Scalable Chemical Production Process

The AGE1.CR and AGE1CR.pIX cell lines were cultivated in the chemically defined medium CD-U2 (produced by Biochrom, Germany, or PAA, Austria) in agitated suspension.

Small scale suspension cultures were performed in vented tubes or flasks in a Multitron (Infors HT, Switzerland) shaking incubator with 5 cm platform amplitude and 180 rpm (tubes) or 150 rpm (flasks) rotation and 8% $CO_2$ atmosphere.

Cultivation in bioreactors at 1 l scale were performed with the cellferm pro (DASGIP, Germany) parallel reactor system. Bioreactor runs at 50 l scale were performed using the disposable SUB 50 system (Hyclone, USA) with a Bioengineering (Switzerland) digital control unit. Default setup was pH of 7.2 units (controlled with 0.5 M NaOH and via $CO_2$ supply), oxygen saturation of 50% and stirring energy input of 12 $W/m^3$. Cultivation in the Wave reactor was performed with the BIOSTAT CultiBag RM (Sartorius, France) programmed for 50% oxygen saturation, pH of 7.2 units, rocking amplitude of 6° and frequency of 12 rocks/min.

For production of highly attenuated pox viruses or alphavirus, cells are cultivated in CD-U2 in 50% of the reactor or vessel volume (for example, 400 ml in the 1 l DASGIP units). Seeding density was 0.8–1×10^6 cells/mL. After three days, cell density was 4–6×$10^6$ cells/mL. One volume of CD-VP4 virus production medium (proprietary, produced by Biochrom) was added and MVA (wildtype ATCCVR-1508) was added directly to the culture. MVA serves as a non-limiting example for illustration purposes; the described development can be applied to other enveloped viruses by somebody skilled in the art.

Isolation of virus was performed by sonification of the infected cell suspension with a Branson S250-D unit powering a 3.2 mm sonifier tip with 10% energy for 45 s for volumes up to 3 mL, or a continuous flow chamber with 100% energy and a flow rate of 0.23 L/min for volumes greater than 400 ml and to demonstrate scalability of the process.

Tangential flow filtration (TFF) was performed with hollow fibre cartridges (GE Healthcare Life Sciences, USA) with an average pore size of 0.1 μM and surface area of 850 $cm^2$. The system parameter were conventional transmembrane pressure of 0.3 bar, flow rate of 10 L/min and shear rate of 6000 $s^{(-1)}$. Intended concentration factor was 10-fold. This is not a critical parameter and any higher or lower concentration factor would be acceptable for purification.

The concentrated suspension was subjected to sonification and the resulting lysate was directly applied or diluted 5-10 fold with 20 mM Tris, pH 8.0, for loading onto an Äkta Explorer System (GE Healthcare) equipped with an experimental affinity membrane adsorber displaying conjugated heparin molecules (Sartorius, pore size >3 μM, adsorption area 250 $cm^2$, bed height of 4 mm, bed volume 7 mL). Prior to sample loading, the membrane adsorber was pre-washed with 250 ml elution buffer (20 mM Tris, pH 8.0, 2 M sodium chloride) and subsequently equilibrated with 250 ml adsorption buffer (20 mM Tris, pH 8.0). After loading, the membrane adsorber was washed with 70 ml running buffer equivalent to 10 membrane bed volumes to remove unbound substances. Purification on affinity membranes serves as a convenient illustration of purification of virus particles produced on a continuous cell line designed for vaccine production. Other methods the present inventors have successfully tested are ion exchange procedures (both cation and anion-exchange) and macroporous materials such as monoliths.

Adsorbed virus particles were eluted by a step gradient using 20 mM Tris buffer, pH 8.0, containing 2 M sodium chloride as the eluent. To achieve complete elution, the membrane adsorber was flushed with 10 bed volumes of eluent at a flow rate of 10 mL/min. The collected elution volume was about 50 mL. The membrane adsorber was used repeatedly via regeneration after each run with 10 bed volumes of 1 M sodium hydroxide.

The entire process was monitored by UV absorption at 280 nm and 260 nm, by dot-blotting against viral antigens, and by dsDNA concentration measurements using Quant-iT PicoGreen dsDNA Kit (Invitrogen, USA) intercalating dye according to the instructions of the manufacturer.

Titration of MVA was performed in Vero cells (African green monkey kidney cells; ATCC CCL-81) in a variation of the immunofocus assay by Reed and Munch as described previously (Jordan, et al. 2009 in Vaccine 27, 748-756).

Figure 2:
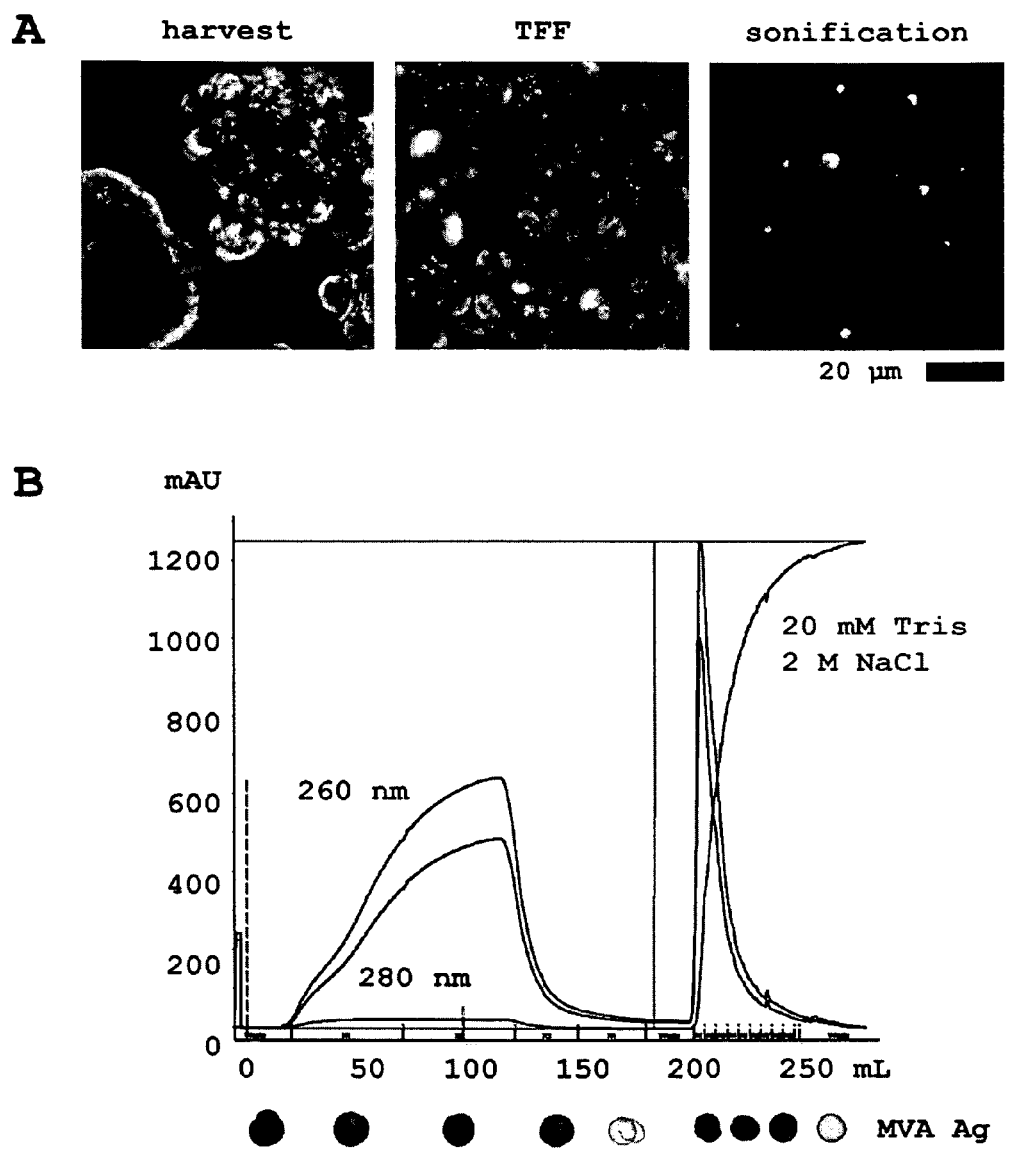
FIG. 2: Demonstration of the downstream process including affinity chromatography. Panel (A) shows culture appearance at harvest of largely intact cells, concentration of such MVA-infected cells by TFF, and lysis by sonification. (B) provides the chromatogram for MVA purification by heparin affinity chromatography. Chromatography was monitored by UV-light absorption and immunoblotting of individual fractions against MVA antigens (blue spots below chromatogram). Panel (C) shows concentrations of and yields for MVA infectious units, total protein and DNA in the load, flow through and pooled elution volumes.
Figure 2:
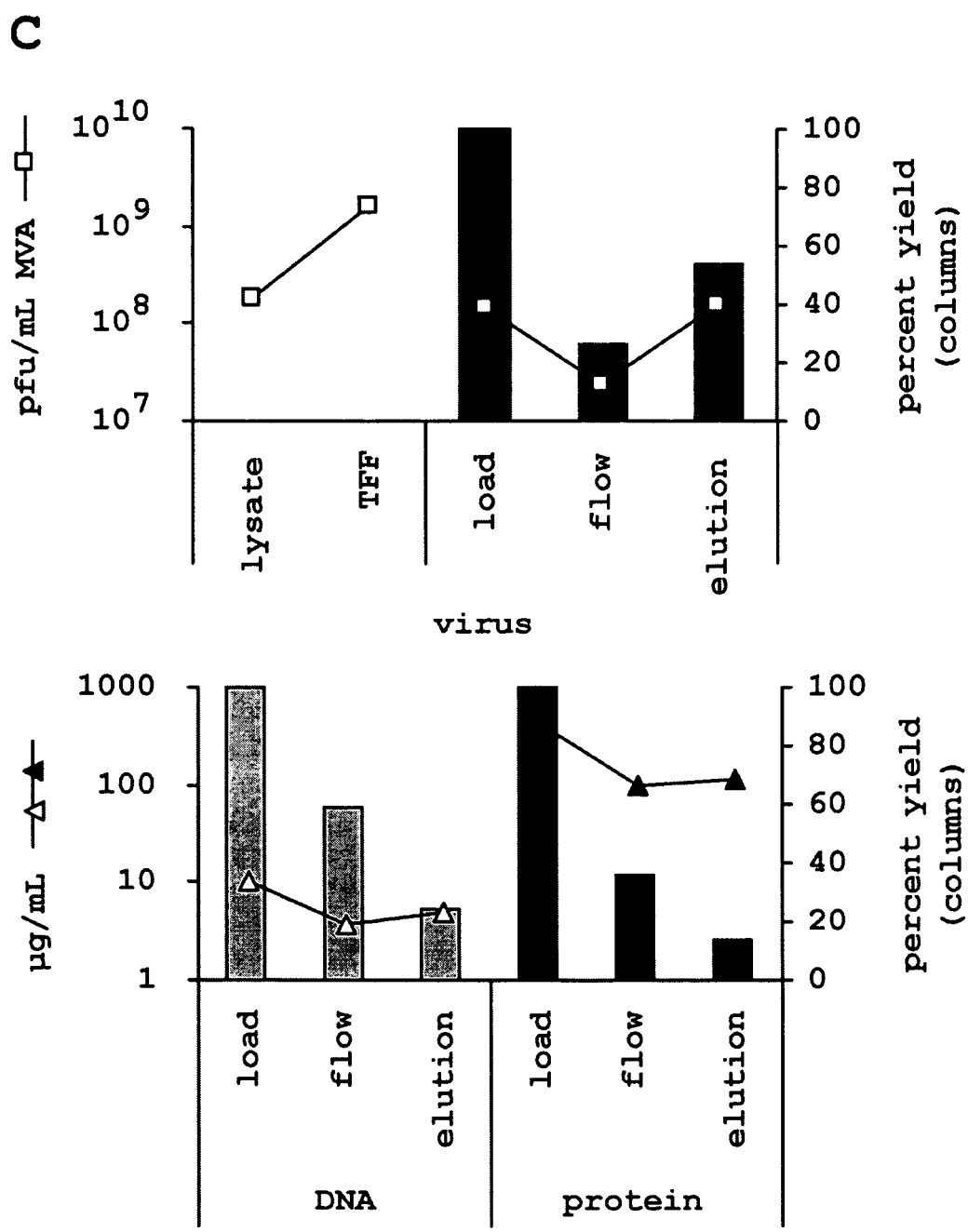

FIG. 1 presents the results from this example and FIG. 2 demonstrates that the described cell suspension can be used for further downstream processing. However, FIG. 2 (C) also demonstrates that the protocol for preparation of lysate from the infected culture must be modified for effective downstream processing. Although affinity chromatography can be performed on the lysate, there is yet insufficient separation of host cell DNA and infectious units in the elution fraction. In this example, the TFF preparation was diluted 10-fold prior chromatography. Assuming a dose of $10^8$ infectious units and 10 ng of DNA in 1 ml vaccine to be applied, the inventors start with 1 vaccine dose in the load fraction and elute 2 vaccine doses. In the same diluted lysate, the inventors start with 1000-fold excess of DNA in the load fraction and elute 500-fold excess of DNA from the column. Thus, the inventors deplete DNA 2-fold and increase virus concentration by the same factor, obtaining a purification factor of 4 and below target by two orders of magnitude. For total protein content, the inventors measure 430 μg/ml in the applied load and 113 μg/ml in the elution fraction; corrected for differences in volumes of the fractions, yield for protein is 13% and depletion therefore 87%.

Example 2

Disruption of Virus:DNA Complexes

To improve depletion of DNA from vaccine preparations, and to remove particulate material interfering with subsequent downstream steps, diatomaceous earth was used as non-inert filtration matrix. Predominantly a powder of amorphous silicon dioxide, the advantage of diatomaceous earth is low cost and consistent supply. This can be a decisive factor for transfer of vaccine production processes to developing or newly industrialized countries where novel and effective vectorial vaccines are urgently needed (Francis 2010 in Biologicals 38, 523-528).

However, diatomaceous earth is also reported to bind and sequester viruses for water purification purposes (Farrah et al. 1991 in Appl Environ Microbiol 57, 2502-2506). Furthermore, binding of DNA requires presence of chaotropic salts such as 4 M guanidine thiocyanate that would kill any viral vector (Carter and Milton 1993 in Nucleic Acids Res 21, 1044). Thus, physical (such as pH, temperature and incubation time) and chemical parameters (from single small molecules to any collection of macromolecules) that cause a mild chaotropic environment and induce selective binding or repulsion of DNA or live viral vector had to be identified. Induction of this environment must be transferable to scalable processes, and must also be compatible with the intended application in veterinary or human medicine.

Use of diatomaceous earth serves as a non-limiting example to demonstrate processes where formation of complexes between virus and host cell DNA is prevented or disrupted, and to demonstrate a purification scheme that would allows separation of DNA from infectious units in further downstream processing. Known to anyone skilled in the art, silica can be further modified (such as coated with silanes) or treated (such as etching with strong acids) to adjust the purification protocol to the mechanism disclosed here. Diatomaceous earth is of non-animal origin and available at purification grades suitable for pharmaceutical application. Silicon dioxide granules and powders remain rigid also under high pressure and therefore our procedure can be scaled to very large production volumes and high flow rates. The diatomaceous earth used in the following examples was Acid Washed Celite 545 NF from Advanced Minerals, USA.

AGE1.CR avian cells were infected with MVA to a MOI of 0.1 in chemically defined media as described in example 1. 48 h post infection, NaBr and KCl were added to 250 mM and 150 mM, respectively, and the culture was sonicated to disrupt infected cells. In a reference experiment, the culture was sonicated without addition of chaotropes, but NaBr and KCl were added after lysis.

Earlier, diatomaceous earth was resuspended in 20 mM Tris (pH 7.2) buffer and allowed to equilibrate for at least 6 h. After determination of DNA content, a volume equivalent of 1 g, 2 g, or 3 g mass of diatoms per mg of DNA were added to the lysates and incubated for 20 min at room temperature. The preferred pH for incubation and subsequent steps is 6.8 to 7.4 units. Thereafter, the suspension was filled into a column sealed at the exit with two glass fibre disc filters of 5 µm and 2 µm pore size (ULTA Disc GF from GE Health Care), respectively. The filtrate was drawn by negative pressure. Washing was performed with 4 matrix volumes of Tris buffer containing NaBr and KCl, and elution with 2 M NaCl in Tris buffer. In small scale experiments with approximately 15 ml of lysate the matrix volume was 2.5 mL.

Figure 3:
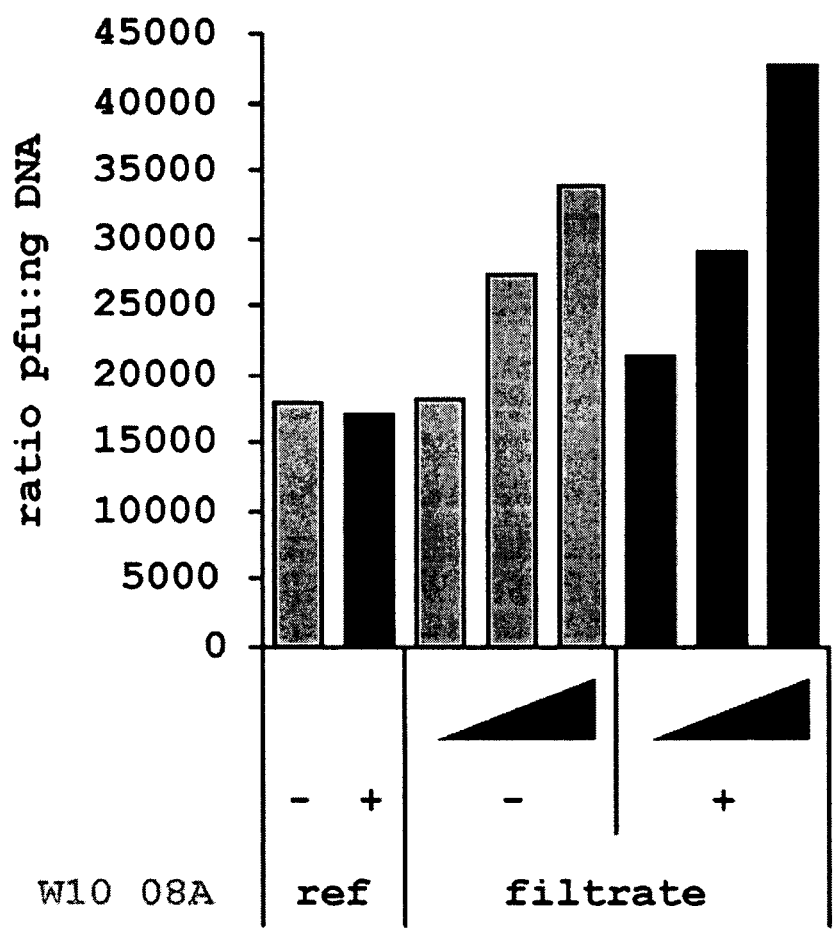
FIG. 3: Demonstration of disruption of virus:DNA complexes. Increasing amount of diatomaceous earth is indicated by the triangle below the abscissa, presence or absence of chaotrope during sonication is indicated by the (+) or (−) symbol. The results of this experiment were converted into ratios of infectious units to ng of DNA. A greater number denotes accumulation of virus and depletion of DNA and is preferred to smaller numbers.

FIG. 3 shows data from this experiment. For a MVA vaccine preparation, the ratio of infectious units to ng of DNA should be at least $10^7$ ($10^8$ infectious units over 10 ng of DNA). In the untreated lysate, the ratio is $1.7 \times 10^4$ for both samples. Silica filtration in the presence of NaBr and KCl improves recovery of virus over DNA. This is a surprising observation as it was expected that chaotropes at such a concentration should inactivate virus.

In the samples sonicated in presence of chaotropes, efficiency of relative DNA depletion is further improved, and the extent of depletion correlates with the amount of silica used in the incubation. At highest mass of silica tested and with sonication in presence of chaotropes one obtains a pfu to DNA ratio of $4.3 \times 10^4$. In the crude lysate the one is 780-fold and in the treated lysate one is only 230-fold removed from target value. The present inventors therefore already present a very efficient initial step in vectorial vaccine preparation and demonstrate importance of prevention of complex formation between contaminant and virion.

Example 3

Diatom Purification

The inventors next optimized diatom purification steps using chemical additives and confirmed the requirement for chaotropes. At the peak of virus production but prior to cytopathic or induced cell lysis, 250 mM NaBr and 150 mM KCl was added to the culture and cell disruption performed by sonication as described above. Additional compounds tested where polyphosphoric acid (as chaotrope), polyvinylpyrrolidone, Tween-20, and dextrane sulfate (as charged or polar polymer). Once having identified the principle of our approach and with the above listing of chemicals it can be deduced by someone skilled in the art that other salts such as NaI or other charged or polar polymers such as chitosan and detergents such as octylphenoxypolyethoxyethanol (NP-40 or IGEPAL) can be used. The masking compounds may interfere with the infectious cycle but timing of addition in the production process as described here allows the use even of substances that bind to a virus.

Figure 4:
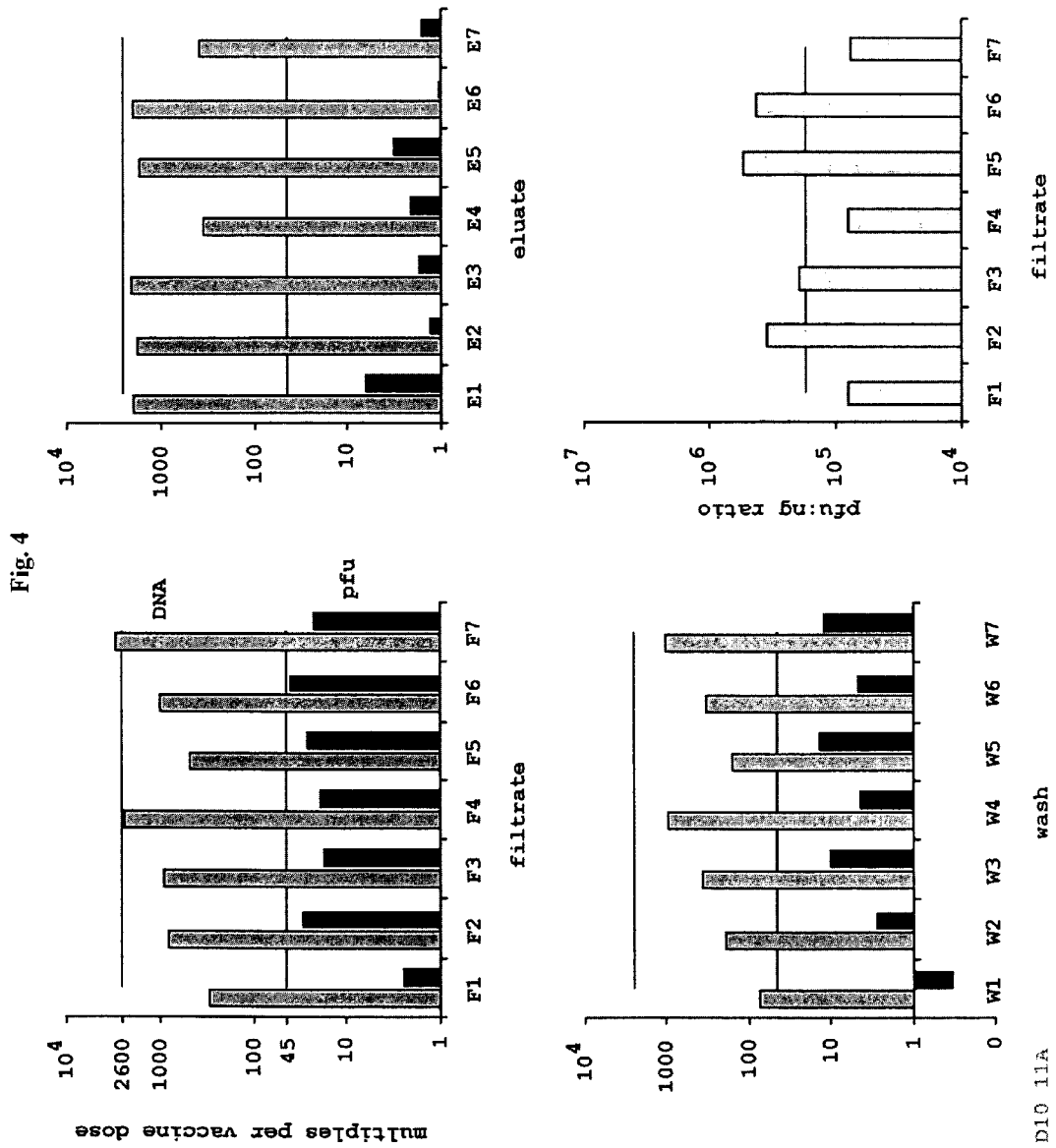
FIG. 4: Demonstration of DNA depletion and virus recovery with diatomaceous earth. The red lines denote level of DNA and the black lines level of pfu in the crude lysate. In the chart in the bottom right corner, the black line denotes ratio of pfu:ng DNA in the crude lysate.
Figure 5:
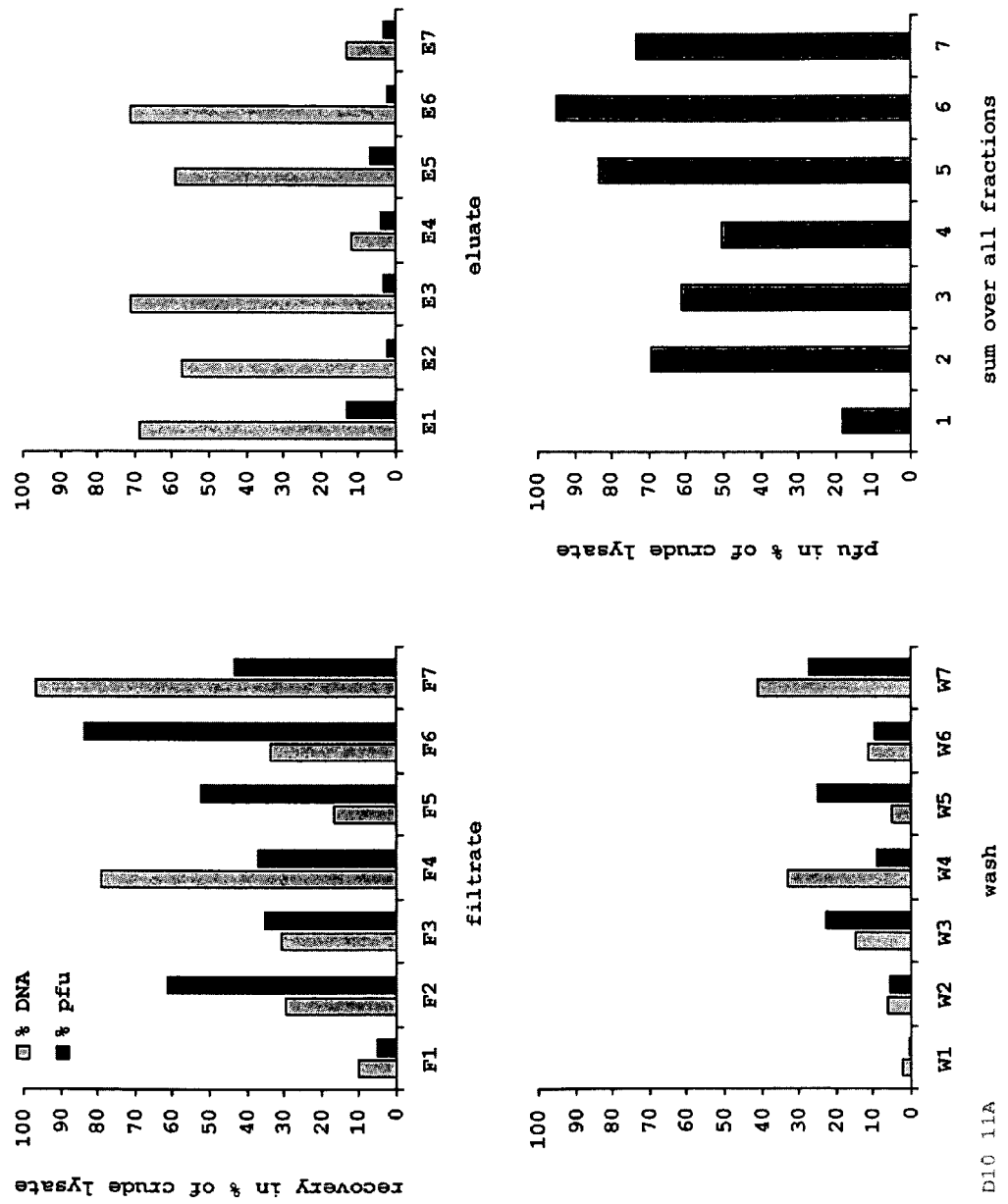
FIG. 5: Presentation of yields from data of the experiment described in FIG. 3.
Figure 6:
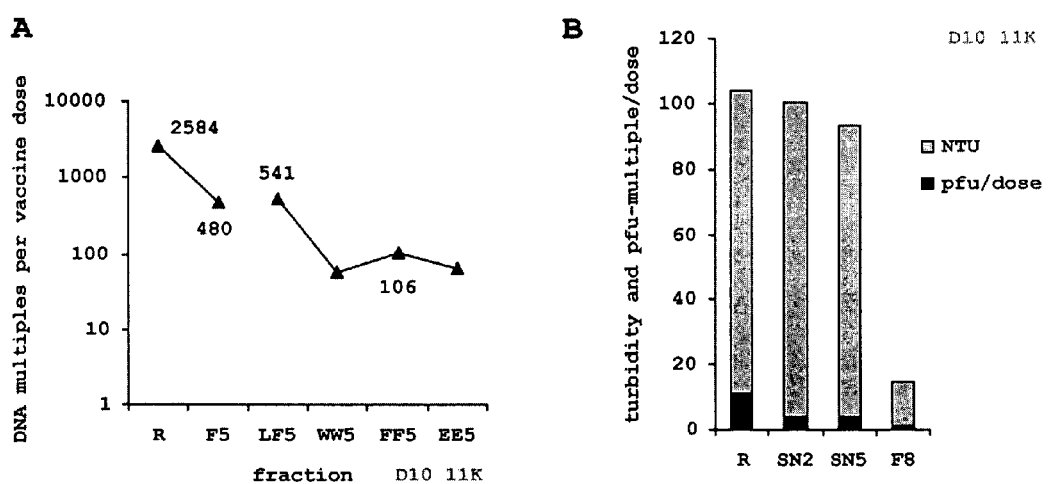
FIG. 6: (A) Further DNA depletion by consecutive filtration, and (B) comparison of turbidity and content of infectious virus in the preparation after centrifugation and after filtration.

FIGS. 4 and 5 provide laboratory data for this example: a culture of CR cells was infected with wild type MVA to 0.1 MOI in the chemically-defined process as described above. 48 h post infection, the infected culture was divided into aliquots that were supplemented with different additives or combinations of additives. One aliquot was left untreated (diluted with PBS) as reference. After supplementation, the aliquots were sonicated and thereafter filtered through diatomaceous earth with 10 g diatoms per mg of DNA as measured in the crude lysate. Infectious units and DNA content were determined in the various filtrate, wash and elution fractions.

The chosen variations in this experiment are (1) sonication and purification without additives; (2) 0.5 mM polyphosphoric acid, NaBr and KCl; (3) 0.025% Tween 20, NaBr and KCl; (4) 2% PVP, NaBr and KCl; (5) NaBr and KCl; (6) 20 mg/L dextran sulfate, NaBr and KCl; and (7) a combination of polysorbate (Tween), PVP, NaBr, and KCl. Where salt was added, the concentration was 250 mM NaBr and 150 mM KCl. In FIGS. 4 and 5, the fractions are abbreviated with F, W and E, and the variations are given by the index so that for example F6 is the filtrate of the aliquot that has been sonicated in presence of dextran sulfate and chaotropes, and E6 is the eluate of the same aliquot.

In FIG. 4, the results are depicted in multiples of vaccine doses at 1 ml volume where one dose should contain at least $10^8$ infectious units but less than 10 ng of DNA. With this standardization, the crude lysate contains a 45-fold excess of MVA and 2600-fold excess of DNA. If the crude lysate without any additive is filtered (column F1), MVA levels drop to 2 vaccine doses and DNA levels to 300-fold of the admissible vaccine level. In WI levels are 0.3-fold for virus and 71-fold for DNA. However, in E1 virus remains at very low 6-fold and DNA at high 2000-fold. The balance could not be closed for pfu recovery (yield as sum over all fractions is only 18%) indicating that virus either was disrupted or infectious units were lost by strong interaction with the silicate. For DNA the balance is 82% with strong binding necessitating purging with 2 M NaCl. The chart in the bottom right corner of FIG. 5 depicts overall recovery of infectious units in all experiments and clearly demonstrates that the present inventors successfully improved reversible binding of virus to the silica in our described variations.

For example, columns for F5 demonstrate that addition of chaotropes facilitates passage of virus so that 25 vaccine doses MVA are recovered in the presence of a 480-fold excess of DNA. In terms of relative yields, 52% of the infectious units but only 17% of the DNA are recovered in F5, 25% of the infectious units are lost in the wash fraction, and 60% of the DNA can be recovered in the elution fraction. These results indicate that the combination of chaotropes and silicate filtration improves the cell culture derived lysate containing a vectorial vaccine virus. This is a surprising observation as the present inventors expected chaotropes, in analogy to the behaviour induced in interaction of DNA with silica, to increase binding to diatomaceous earth.

Already in F5 the present inventors have increased the ratio of pfu:ng DNA (as discussed in the previous example) from $1.7 \times 10^5$ to $5.3 \times 10^5$; the distance to target value of $10^7$ is decreased from 60-fold to less than 20-fold.

Based on F5, other additives were tested to improve DNA binding or virus passage. The results shown in F4 and F7 were another surprise: presence of PVP prevents interaction of diatoms with DNA to such an extent that already in the filtrate 80% to 95% of the DNA is recovered. Although undesirable in the context of example 3, this discovery points to application of PVP in further downstream purification with affinity matrix: there, virus is allowed to adsorb to the matrix and binding of DNA is inhibited by the presence of PVP. After a wash step, virus is eluted and the amount of DNA available for co-elution is reduced.

The inventors have also fortuitously discovered a substance that selectively allowed DNA to adsorb to the diatoms but infectious units to pass into the filtrate. The addition of dextrane sulfate together with NaBr and KCl as shown in F6 resulted in >80% yield for infectious units but only 34% yield for DNA in the filtrate. Conversely, in the eluate E6, 71% of the DNA and 2% of the pfu are recovered.

Interestingly, the wash fraction W6 still contains approximately 10% each of virus and DNA. This indicates that the capacity of the diatoms for DNA has been exhausted and suggests that an additional filtration step of F6 using the same or similar conditions will further reduce the unwanted DNA content of the preparation. Alternatively, one could increase the amount of diatoms to be used in the first filtration step.

Example 4

Sequential Filtration

The inventors next examined whether the method described here can be applied sequentially to further improve DNA depletion. Based on the previous example, sample F5 therein was subjected to the described filtration with 10 g diatoms per mg of DNA as determined in the crude lysate, the load towards F5. In FIG. 6 (A) the crude lysate is denoted with R. In this sample, the amount of DNA is 2584-fold in excess of an admissible 1 ml vaccine dose. After filtration and reported in FIG. 5 as F5, the excess is reduced to 541-fold. After a second such filtration, shown as FF5 in FIG. 6 (A), the excess is further reduced to 106-fold. The other samples shown in FIG. 6 (A) are LF5 for the load for the second filtration (identical to F5), WW5 for wash of second filtration, and EE5 for eluate of second filtration.

In summary, the inventors demonstrate a 24-fold (2584/106) combined reduction in DNA content, which is impressive considering that this initial step in vaccine purification is performed without enzymatic digestion.

Example 5

Turbidity

As summarized above, for a live vaccine maintenance of infectivity in the purification is a most complicated challenge. Separation of contaminants such as host-cell DNA or protein from the fragile viral particles requires further downstream processing, usually including tangential flow filtration, affinity chromatography or membrane adsorption. Resolution, efficiency and yields of such methods improve with clarity of the suspension containing the virus. The reason is that haziness or turbidity in a solution indicates presence of undesired particles that may block pores and compete with virus for binding sites to the immobile phase.

To demonstrate the surprising suitability of the diatom filtration step for further downstream processing, the inventors also quantified turbidity of a filtrate prepared according to example 3 using the Turbiquant 1100 IR (Merck Chemicals Germany). This device measures presence of suspended particles in Nephelometric Turbidity Units (NTU) via scattering of light relative to calibration standards provided by the manufacturer.

In FIG. 6 (B), filtrate and centrifugation supernatants are compared in turbidity and virus content. Turbidity in NTU is shown by the light bars and pfu-multiples per 1 mL vaccine dose are shown by the dark bars. R denotes a lysate obtained by sonication in presence of 250 mM NaBr and 150 mM KCl but without further purification treatment. SN2 and SN5 denote the supernatant of centrifugation with 200×g and 500×g, respectively, and F8 denotes the diatom filtrate.

As predicted, even gentle centrifugation with 200×g removes a significant fraction of the infectious units into the pellet, and even more forceful centrifugation with 500×g does not provide a significantly less turbid supernatant. However, filtration as described here reduces turbidity to 13% while still maintaining adequate numbers of infectious to continue with further downstream processing.

CITED DOCUMENTS

[1] Zurbriggen, S., Tobler, K., Abril, C. et al. Isolation of sabin-like polioviruses from wastewater in a country using inactivated polio vaccine. *Appl Environ Microbiol* 2008, 74(18), 5608-5614.
[2] Marris, E. Dramatic rescue relieves rare case of smallpox infection. *Nat Med* 2007, 13(5), 517.
[3] Parrino, J. & Graham, B. S. Smallpox vaccines: Past, present, and future. *J Allergy Clin Immunol* 2006, 118(6), 1320-1326.
[4] Excler, J. L., Parks, C. L., Ackland, J., Rees, H., Gust, I. D. & Koff, W. C. Replicating viral vectors as HIV vaccines:

Summary report from the IAVI-sponsored satellite symposium at the AIDS vaccine 2009 conference. *Biologicals* 2010, 38(4), 511-521.

[5] Plotkin, S. A. Vaccines: the fourth century. *Clin Vaccine Immunol* 2009, 16(12), 1709-1719.

[6] Cebere, I., Dorrell, L., McShane, H. et al. Phase I clinical trial safety of DNA- and modified virus Ankara-vectored human immunodeficiency virus type 1 (HIV-1) vaccines administered alone and in a prime-boost regime to healthy HIV-1-uninfected volunteers. *Vaccine* 2006, 24(4), 417-425.

[7] Dorrell, L., Williams, P., Suttill, A. et al. Safety and tolerability of recombinant modified vaccinia virus Ankara expressing an HIV-1 gag/multiepitope immunogen (MVA. HIVA) in HIV-1-infected persons receiving combination antiretroviral therapy. *Vaccine* 2007, 25(17), 3277-3283.

[8] Jin, X., Ramanathan, M., Jr., Barsoum, S. et al. Safety and immunogenicity of ALVAC vCP1452 and recombinant gp160 in newly human immunodeficiency virus type 1-infected patients treated with prolonged highly active antiretroviral therapy. *J Virol* 2002, 76(5), 2206-2216.

[9] Webster, D. P., Dunachie, S., Vuola, J. M. et al. Enhanced T cell-mediated protection against malaria in human challenges by using the recombinant poxviruses FP9 and modified vaccinia virus Ankara. *Proc Natl Acad Sci USA* 2005, 102(13), 4836-4841.

[10] Drillien, R., Spehner, D. & Hanau, D. Modified vaccinia virus Ankara induces moderate activation of human dendritic cells. *J Gen Virol* 2004, 85(Pt 8), 2167-2175.

[11] Liu, L., Chavan, R. & Feinberg, M. B. Dendritic cells are preferentially targeted among hematolymphocytes by Modified Vaccinia Virus Ankara and play a key role in the induction of virus-specific T cell responses in vivo. *BMC Immunol* 2008, 9, 15.

[12] Ryan, E. J., Harenberg, A. & Burdin, N. The Canarypoxvirus vaccine vector ALVAC triggers the release of IFN-gamma by Natural Killer (NK) cells enhancing Th1 polarization. *Vaccine* 2007, 25(17), 3380-3390.

[13] Sutter, G. & Moss, B. Nonreplicating vaccinia vector efficiently expresses recombinant genes. *Proc Natl Acad Sci USA* 1992, 89(22), 10847-10851.

[14] Sutter, G., Wyatt, L. S., Foley, P. L., Bennink, J. R. & Moss, B. A recombinant vector derived from the host range-restricted and highly attenuated MVA strain of vaccinia virus stimulates protective immunity in mice to influenza virus. *Vaccine* 1994, 12(11), 1032-1040.

[15] Coulibaly, S., Bruhl, P., Mayrhofer, J., Schmid, K., Gerencer, M. & Falkner, F. G. The nonreplicating smallpox candidate vaccines defective vaccinia Lister (dVV-L) and modified vaccinia Ankara (MVA) elicit robust long-term protection. *Virology* 2005, 341(1), 91-101.

[16] Gilbert, S. C., Moorthy, V. S., Andrews, L. et al. Synergistic DNA-MVA prime-boost vaccination regimes for malaria and tuberculosis. *Vaccine* 2006, 24(21), 4554-4561.

[17] Rotz, L. D., Dotson, D. A., Damon, I. K. & Becher, J. A. Vaccinia (smallpox) vaccine: recommendations of the Advisory Committee on Immunization Practices (ACIP), 2001. *MMWR Recomm Rep* 2001, 50(RR-10), 1-25; quiz CE21-27.

[18] Monto, A. S., Maassab, H. F. & Bryan, E. R. Relative efficacy of embryonated eggs and cell culture for isolation of contemporary influenza viruses. *J Clin Microbiol* 1981, 13(1), 233-235.

[19] White, D. O. & Fazekas De St Groth, S. Variation of host resistance to influenza viruses in the allantois. *J Hyg (Lond)* 1959, 57(1), 123-133.

[20] Philipp, H. C. & Kolla, I. Laboratory host systems for extraneous agent testing in avian live virus vaccines: problems encountered. *Biologicals* 2010, 38(3), 350-351.

[21] Enserink, M. Influenza. Crisis underscores fragility of vaccine production system. *Science* 2004, 306(5695), 385.

[22] Jordan, I., Vos, A., Beilfuss, S., Neubert, A., Breul, S. & Sandig, V. An avian cell line designed for production of highly attenuated viruses. *Vaccine* 2009, 27(5), 748-756.

[23] Manohar, M., Orrison, B., Peden, K. & Lewis, A. M., Jr. Assessing the tumorigenic phenotype of VERO cells in adult and newborn nude mice. *Biologicals* 2008, 36(1), 65-72.

[24] Cyrklaff, M., Risco, C., Fernandez, J. J. et al. Cryo-electron tomography of vaccinia virus. *Proc Natl Acad Sci USA* 2005, 102(8), 2772-2777.

[25] Francis, D. P. Successes and failures: Worldwide vaccine development and application. *Biologicals* 2010, 38(5), 523-528.

[26] Farrah, S. R., Preston, D. R., Toranzos, G. A., Girard, M., Erdos, G. A. & Vasuhdivan, V. Use of modified diatomaceous earth for removal and recovery of viruses in water. *Appl Environ Microbiol* 1991, 57(9), 2502-2506.

[27] Carter, M. J. & Milton, I. D. An inexpensive and simple method for DNA purifications on silica particles. *Nucleic Acids Res* 1993, 21(4), 1044.

The invention claimed is:

1. A method of virus purification comprising the steps of
   (i) incubating a virus producing cell with at least one chaotropic salt selected from the group consisting of NaBr at a concentration of at least 75 mM and KCl at a concentration of at least 75 mM prior to cell lysis,
   (ii) lysing said virus producing cell after the incubating of step (i), and
   (iii) separating said virus from at least part of the non-viral substances comprised in said virus producing cell or its cell culture medium.

2. The method of claim 1, wherein step (iii) is carried out by filtration over a siliceous substance.

3. The method of claim 1, wherein said at least one chaotropic salt is added at the time of cell infection with the virus, immediately after said infection, or at the time of peak virus production.

4. The method of claim 1, wherein said at least one chaotropic salt is administered in combination with urea.

5. The method of claim 1, wherein said virus is an enveloped virus, an attenuated virus, a replication deficient virus and/or a live vaccine.

6. The method of claim 1, wherein said non-viral substances are polynucleotides, host cell protein, or medium additives used in host cell cultivation or virus production.

7. The method of claim 2, wherein said siliceous substance is selected from the group consisting of diatomaceous earth, acid washed diatomaceous earth, acid etched diatomaceous earth, or diatomaceous earth treated with a silane.

8. The method of claim 1, wherein the virus producing cell is incubated with NaBr at a concentration of at least 75 mM and KCl at a concentration of at least 75 mM.

9. The method of claim 8, wherein the virus producing cell is incubated with NaBr at a concentration of between 75 mM and 750 mM and KCl at a concentration of between 75 mM and 750 mM.

10. The method of claim 8, wherein the virus producing cell is incubated with NaBr at a concentration of between 100 mM and 550 mM and KCl at a concentration of between 75 and 500 mM.

11. The method of claim 8, wherein the virus producing cell is incubated with NaBr at a concentration of between 150 mM and 450 mM and KCl at a concentration of between 105 mM and 400 mM.

12. The method of claim 8, wherein step (iii) is carried out by filtration over a siliceous substance.

13. The method of claim 1, wherein the incubating further comprises incubating the virus producing cell with dextrane sulphate, polyphosphoric acid, polyvinylpyrrolidon, NaI, chitosan, and/or detergents prior to cell lysis.

14. The method of claim 1, wherein the incubating further comprises incubating the virus producing cell with dextrane sulphate, polyphosphoric acid, and/or polysorbate prior to cell lysis.

15. The method of claim 1, wherein the incubating further comprises incubating the virus producing cell with dextrane sulphate and/or polyphosphoric acid prior to cell lysis.

* * * * *